US010849505B2

(12) United States Patent
Muschaweck et al.

(10) Patent No.: US 10,849,505 B2
(45) Date of Patent: Dec. 1, 2020

(54) ELECTRONIC MICROSCOPE

(71) Applicant: Arnold & Richter Cine Technik GmbH & Co. Betriebs KG, Munich (DE)

(72) Inventors: Julius Muschaweck, Gauting (DE); Hans Kiening, Lengries (DE); Patrick Burckstummer, Munich (DE); Peter Geissler, Munich (DE)

(73) Assignee: ARNOLD & RICHTER CINE TECHNIK GMBH & CO. BETRIEBS KG, Munich (DE)

(*) Notice: Subject to any disclaimer, the term of this patent is extended or adjusted under 35 U.S.C. 154(b) by 164 days.

(21) Appl. No.: 15/847,607

(22) Filed: Dec. 19, 2017

(65) Prior Publication Data

US 2018/0368690 A1  Dec. 27, 2018

(30) Foreign Application Priority Data

Dec. 22, 2016  (DE) .................. 10 2016 125 524

(51) Int. Cl.
*A61B 5/00* (2006.01)
*G02B 21/00* (2006.01)
(Continued)

(52) U.S. Cl.
CPC ........ *A61B 5/0075* (2013.01); *A61B 1/00186* (2013.01); *A61B 1/0646* (2013.01);
(Continued)

(58) Field of Classification Search
CPC .................. A61B 5/0075; A61B 5/0059–0091
See application file for complete search history.

(56) References Cited

U.S. PATENT DOCUMENTS 5,590,660 A  1/1997 MacAulay et al.
6,166,496 A  12/2000 Lys et al.
(Continued)

FOREIGN PATENT DOCUMENTS

DE  10242983 A1  3/2004
WO  2015/185662 A2  12/2015
WO  2016/033590 A1  3/2016

OTHER PUBLICATIONS

Brochure "ARRISCOPE—A new era in surgical microscopy" (English version).

*Primary Examiner* — Robert J Hance
(74) *Attorney, Agent, or Firm* — Amster, Rothstein & Ebenstein LLP

(57) ABSTRACT

An electronic microscope has an electronic image sensor for generating primary image data sets, wherein the image sensor is configured to generate image signals that correspond to a plurality of different reception spectra, and wherein each primary image data respectively comprises at least one image signal of each of the plurality of reception spectra for a plurality of image zones. A control device of the microscope is configured to control an illumination device to make a cyclically repeating transmission of electromagnetic radiation having a plurality of different illumination spectra and to control the image sensor to generate a respective primary image data set for each of the plurality of different illumination spectra. A processing unit of the microscope is configured to calculate the reflection spectrum from the generated primary image data sets for at least some of the plurality of image zones and, starting from the primary image data sets generated for the plurality of different illumination spectra, to determine at least one secondary image data set in dependence on the calculated reflection spectrum, said secondary image data set being at least partly modified with respect to the primary image data sets.

20 Claims, 2 Drawing Sheets

(51) Int. Cl.
  *A61B 90/20*  (2016.01)
  *G02B 21/36*  (2006.01)
  *A61B 1/00*   (2006.01)
  *A61B 1/06*   (2006.01)
  *G01J 3/10*   (2006.01)
  *G01J 3/28*   (2006.01)
  *A61B 17/00*  (2006.01)

(52) U.S. Cl.
  CPC ............ *A61B 1/0684* (2013.01); *A61B 90/20* (2016.02); *G01J 3/10* (2013.01); *G01J 3/2823* (2013.01); *G02B 21/0012* (2013.01); *G02B 21/367* (2013.01); *A61B 2017/00061* (2013.01)

(56) References Cited

U.S. PATENT DOCUMENTS

| | | |
|---|---|---|
| 6,293,911 B1 | 9/2001 | Imaizumi et al. |
| 6,898,458 B2 * | 5/2005 | Zeng .................... G01J 3/0289 600/476 |
| 7,580,185 B2 | 8/2009 | Haisch et al. |
| 8,100,826 B2 | 1/2012 | MacKinnon et al. |
| 2004/0225222 A1 | 11/2004 | Zeng et al. |
| 2007/0036430 A1 * | 2/2007 | Katsumata ............ G01J 3/463 382/162 |
| 2009/0023991 A1 * | 1/2009 | Gono ................ A61B 1/00009 600/109 |
| 2009/0318815 A1 * | 12/2009 | Barnes ................ A61B 5/0064 600/473 |
| 2010/0056928 A1 | 3/2010 | Zuzak et al. |
| 2013/0012794 A1 * | 1/2013 | Zeng .................... H04N 5/332 600/328 |
| 2014/0193050 A1 | 7/2014 | Miller |
| 2015/0250387 A1 | 9/2015 | Hauger et al. |
| 2016/0022119 A1 * | 1/2016 | Shahmoon ......... A61B 1/00167 600/182 |

* cited by examiner

ELECTRONIC MICROSCOPE

The present invention relates to an electronic microscope having at least one electronic image sensor for generating image data sets, having an imaging optics for generating an image of an object arranged in a recording zone of the microscope on the image sensor, and having an electronic viewfinder for displaying an image corresponding to a respective image data set.

Such a microscope is in particular used as an operating microscope to increase the quality of invasive medical interventions (operations) in comparison with conventional, non-electronic microscopes.

Although electronic operating microscopes already have a good representation capability, there is a desire to further improve the representation capability, i.e. the image or electronic representation of the object presented to the user should be improved. There is in particular the need to improve the representation capability while taking account of subjective perception criteria and/or objective object properties. For example, the perceived information content of the visual representation should be increased in dependence on the nature of a surgical site (e.g. visual properties and/or geometrical dimensions). There is furthermore the need to be able to select the information content of the visual representation at the electronic viewfinder in dependence on a surgical task or on a development of the surgery.

An obstacle to increasing the visual information acquisition and the corresponding representation of an increased or selected information content at the electronic viewfinder can be found in the conflict between the number of the spectral channels provided at the image sensor and the number of available illumination spectra, on the one hand, and the desired spatial and temporal resolution, that should be as high as possible, and the brightness sensitivity of the image sensor as well as the tolerable heating of the object being observed due to illumination, on the other hand.

It is an object of the invention to provide an electronic microscope of the initially named kind that has an improved representation capability, in particular an increased information content and/or an information content of the visual representation that can be influenced by a user of the microscope.

The object of the invention is satisfied by an electronic microscope having the features of claim 1.

The microscope in accordance with the invention comprises at least one electronic image sensor for generating primary image data sets, an imaging optics, an electronic viewfinder, an illumination device, a control device, a memory, and a processing unit.

The at least one electronic image sensor is configured to generate image signals that correspond to a plurality of different reception spectra. Two, preferably at least three or four, different reception spectra and respective associated image signals can be provided, for example (e.g. for the colors red, green, and blue). "Reception spectrum" is to be understood as the spectral sensitivity of the image sensor with respect to the associated image signal. The image signals generated for the respective image zone and corresponding to the plurality of different reception spectra are preferably generated at least substantially simultaneously. It is generally also possible, however, to generate these image signals consecutively in time, in particular with static objects or with objects that only move relatively slowly (in comparison with a frame speed of the image sensor).

Each primary image data set comprises at least one respective image signal, preferably exactly one image signal, of each of the plurality of reception spectra for a plurality of image zones, i.e. the image signals of all the reception spectra are present for every image zone. A respective image signal can either correspond to an actually recorded picture element or can be interpolated from a plurality of picture elements, with a respective image zone being able to comprise one or more picture elements. With an image sensor having a Bayer color filter matrix, for example, four respective picture elements which are arranged next to one another and with which the color filters or reception spectra green, red, green and blue are associated form an image zone. Alternatively to this, a plurality of image sensors having different spectral sensitivities (e.g. red, green, and blue) can also be provided that each only receive a portion of the received radiation by means of a beam splitter, with the respective picture elements, however, being arranged in geometrical agreement with one another with respect to the optical reception path so that the respective image zone only extends over one picture element. The respective image zone also only comprises one picture element with a so-called Foveon image sensor in which three image signals for different reception spectra (red, green, and blue) are intrinsically generated.

The imaging optics serves for generating an image of an object arranged in a reception zone of the microscope on the image sensor. The term "object" is to have a broad interpretation. In particular zones that are the subject of a medical intervention represent objects in the sense of the invention. Tissue samples that are the subject of a histological examination equally represent objects.

The electronic viewfinder represents the optically visual interface for the user of the microscope. The electronic viewfinder can in particular comprise an electronic display apparatus (a display, for example) having an upstream eyepiece. The electronic viewfinder can in particular be configured as an electronic binocular eyepiece for a stereoscopic microscope. The electronic viewfinder can, however, also comprise a 2D or 3D monitor that can be observed simultaneously by a plurality of persons.

The illumination device is configured to transmit electromagnetic radiation having a variable illumination spectrum into the recording zone. The electromagnetic radiation can have a visible wavelength or an invisible wavelength. The wavelength can in particular also be in the infrared or ultraviolet range.

The control device is configured to control the illumination device to make a cyclically repeating transmission of the electromagnetic radiation having a plurality of different illumination spectra during a respective illumination cycle and to control the at least one image sensor to generate a respective primary image data set for each of the plurality of different illumination spectra. An illumination cycle preferably comprises at least three, in particular four or five, different illumination spectra that are transmitted repeatedly consecutively in time and in a repeating order. The respective illumination spectrum can substantially comprise a wavelength or a wavelength range. The plurality of different illumination spectra can be disjunctive with respect to one another and be spectrally spaced apart from one another and can be adjacent to one another or overlap one another. The different illumination spectra can in particular comprise a plurality of visible colors that are different from one another. While the object arranged in the recording zone of the microscope is consecutively subjected to the electromagnetic radiation of the plurality of different illumination spectra, the image sensor generates an associated primary image data set for every illumination spectrum, that is at least one respective image signal of each of the plurality of reception spectra for each image zone. Image signals of the different reception spectra are thus present for each illumination spectrum, and indeed for each of the plurality of (geometrical) image zones.

A computing rule is stored in the memory that is based on the particular circumstances of the electronic microscope and in particular takes account of the different reception spectra and illumination spectra. The computing rule represents a reflection spectrum of a respective image zone in dependence on the image signals that have been generated for the respective image zone for each of the different reception spectra with respect to each of the plurality of different illumination spectra. In other words, as will be explained in more detail in the following, the computing rule allows an at least substantially complete reflection spectrum to be calculated at least approximately from the corresponding image signals on the basis of the respective combination of a plurality of different reception spectra with a plurality of different (suitably selected) illumination spectra, said reflection spectrum also comprising spectral ranges that do not directly coincide with the different reception spectra or illumination spectra.

A plurality of different response functions are therefore obtained by the generation of measured values with respect to the different combinations of reception spectrum and illumination spectrum, said response functions allowing the respective reflection spectrum to be calculated approximately—but with high accuracy and below the perceptibility threshold of the human eye—with the calculated reflection spectrum also being able to comprise one or more spectral ranges that are outside the plurality of different illumination spectra and reception spectra. For example, twelve such response functions can be determined and evaluated by using four different illumination spectra and three different reception spectra within an illumination cycle provided that all of these response functions differ from zero and are linearly independent of one another.

Said calculated reflection spectrum can in particular extend over a spectral range that extends substantially from the lowest wavelength that is covered by the different reception spectra and illumination spectra up to the highest wavelength that is covered by the different reception spectra and illumination spectra.

Said reflection spectrum generally describes the dependency of the degree of reflection on the wavelength over a spectral range. The degree of reflection is generally defined as the ratio of reflected intensity to incident intensity of the electromagnetic radiation. The degree of reflection can therefore be the ratio of the radiation intensity reflected at the object zone to the radiation intensity received from the illumination device at the object zone with respect to the object zone corresponding to the observed image zone.

Said computing rule thus indicates how the reflection spectrum of a respective object zone can be approximated in dependence on the image signals of the observed image zone while taking account of all of the plurality of primary image data sets of an illumination cycle.

The processing unit is configured to calculate the respective reflection spectrum for at least some of the plurality of image zones using the stored computing rule from the primary image data sets generated for the plurality of different illumination spectra. The processing unit is further configured to determine, starting from the primary image data sets generated for the plurality of different illumination spectra, at least one secondary image data set in dependence on the calculated reflection spectrum of the respective image zone, the secondary image data set being at least partly modified with respect to the primary image data sets. This can in particular be done in real time during the operation of the electronic microscope, that is while the user observes a correspondingly determined or assembled image at the electronic viewfinder. The determined secondary image data set can in particular represent an illumination spectrum that differs from the plurality of different illumination spectra. In other words, the determined secondary image data set can correspond to a "virtual illumination spectrum" that differs from the actually used illumination spectra of the illumination device.

The control device is furthermore configured to control the electronic viewfinder to display an image corresponding to the secondary image data set.

The fact is utilized for the determination and visual representation of said secondary image data set that hyperspectrally resolved reflection spectra can be approximated by means of the multispectrally resolved primary image data sets cyclically recorded with different illumination spectra and can be used to generate at least one secondary image data set from the primary image data sets that can be displayed at the electronic viewfinder. The reflection spectrum of the observed object provides valuable information on the properties of the object (such as a chemical or biochemical composition) that can be used in different ways, as will be explained more precisely in the following. This information can be represented at the electronic viewfinder of the microscope in that the primary data sets generated by means of the image sensor are correspondingly modified, with this being able to be done in dependence on the application and on the objective for some or all of the plurality of image zones as well as for one, more or all of the different primary image data sets that correspond to the different illumination spectra of a respective illumination cycle.

The control device, the memory, and the processing unit of the electronic microscope as well as also the selection device named in the following and the evaluation device of the electronic microscope can be partly or completely formed by a single electronic unit (e.g. a microprocessor).

Advantageous embodiments of the invention are named in the following and in the dependent claims as well as shown in the drawings.

In accordance with an embodiment, a desired observation spectrum can be selected by means of a selection device, in particular manually or automatically, with the secondary image data set being modified with respect to the primary image data sets on the basis of the selected observation spectrum. In this respect, the secondary image data set for the at least some image zones can represent the reflection capability of the object arranged in the recording zone within the selected observation spectrum. In other words, the selected observation spectrum in this embodiment represents the basis for a "virtual spectral filtering" of the primary image data sets. As explained, the processing unit of the electronic microscope calculates the respective reflection spectrum for some or all of the image zones from the primary image data sets generated for the plurality of different illumination spectra in accordance with the stored computing rule. Said selection of a desired observation spectrum thus means that the corresponding secondary image data set only comprises a spectral portion of the calculated (complete) reflection spectrum to represent the reflection capability of the observed object (in the respective image zone) for this selected spectral portion. The content of a respective primary image data set in the spectral range can in particular be correspondingly changed by amplifying and/or attenuating specific spectral portions (e.g. by means of one or more bandpasses or evaluation functions). Specific details of the imaged object can hereby e.g. be made more visible or differentiable for the human eye and/or the visual reproduction can be designed as subjectively more pleasant.

In this connection, the determined secondary image data set shown visually at the electronic viewfinder can represent the reflection capability of the object within the selected observation spectrum. The correspondingly selected observation spectrum can in this manner improve the visibility of the observed object such that object zones having different degrees of reflection are also actually reproduced in a visually distinguishable manner. This is particularly useful in the case of use as an operating microscope since the surgeon can better distinguish different types of tissue. For example, blood low in oxygen and blood rich in oxygen can also be better distinguished from one another.

The selection of the observation spectrum (i.e. of the "virtual spectral filter") can be specified by a user and/or can be carried out automatically by the control device of the microscope using predefined criteria. A specific observation spectrum can also be preset that is only modified as required by the user. A respective observation spectrum can also be changed by a user, e.g. by settable parameters. The selection device can comprise an input device for a manual specification of the desired observation spectrum. The input device can, for example, have a selection button, a slide control, a rotary actuator, or a numerical pad for a numerical input, with such an input service being able to be provided physically and/or virtually (in particular at the electronic viewfinder or at a separate display, e.g. by mouse click or as a touch function). The selection of the desired observation spectrum can in particular take place during the operation of the electronic microscope.

In accordance with a further embodiment, the calculated reflection spectrum of the respective image zone can be evaluated with respect to at least one property of the object by means of an evaluation device of the electronic microscope, with the secondary image data set being modified relative to the primary image data sets on the basis of at least one evaluated object property. The determined secondary image data set can thus in particular represent the at least one evaluated object property for the respective image zones.

A named property of the object can in particular be an object kind or an object type. Furthermore, object zones or object outlines can be properties of objects that are detected by the evaluation device. Further examples for object properties are the color, size, and surface quality.

An object property can in particular be a type of tissue with respect to the use as an operating or medical microscope. In other words, the calculated reflection spectrum is used to answer the question as to which type of tissue (e.g. nerve tissue, muscle tissue, fat tissue, connective tissue, in particular including bones and cartilage) is imaged in the observed image zone. A tissue classification is thus carried out on the basis of the calculated reflection spectrum. Furthermore, malignant types of tissue (e.g. tumor tissue) can be distinguished from benign types of tissue. To determine such medical object properties, a respective reflection spectrum, i.e. a reflection spectrum calculated for a respective image zone, can be compared with a plurality of reflection spectra stored in the microscope for which the respective type of tissue is known. It can then e.g. be determined by means of a spectral interval measurement or by means of a mathematical comparison which of the stored reflection spectra the calculated reflection spectrum comes closest to. If the spectral interval falls below a threshold value, it can be assumed that the reflection spectrum calculated for the observed image zone represents the known type of tissue of the respective stored reflection spectrum.

Depending on the types of tissue or on the medically relevant properties determined for a plurality of image zones, one or more of the primary image data sets can then be modified such that the different types of tissue can be better distinguished from one another visually. Types of tissue of particular interest that have to be particularly observed (e.g. tumor tissue) can in particular be made visible by color or by spectrum or by suitable superposed markings. As the skilled person recognizes, there are a number of possibilities for improving the distinguishability of the different types of tissue or to visually encode object properties. A false-color representation of those image zones for which a specific type of tissue has been identified is also e.g. conceivable. Alternatively, only the outlines of the type of tissue can be marked.

It is understood that the reflection spectrum of the respective image zone can be determined again at regular time intervals. Dynamic object changes such as are in particular to be expected in the case of operations can hereby be taken into account.

The modification of the primary image data sets can be set on the basis of the at least one object property due to the variety of possibilities for achieving a "differentiated" information content of the visual representation at the electronic viewfinder. The user can, for example, choose between a plurality of preset modification variants or specify parameters of the modification. It is hereby particularly easily possible to take account of the individual preferences of the user with respect to the reproduction possibilities.

In accordance with a further embodiment, said selection device is adapted to select the observation spectrum automatically on the basis of the at least one object property. In other words, the microscope can automatically "adapt" to the object to achieve a spectrally better differentiated visual representation.

As already mentioned, the processing unit calculates the respective reflection spectrum for at least some of the plurality of image zones from the primary image data sets generated for the plurality of different illumination spectra in accordance with the stored computing rule. In accordance with an embodiment, the processing unit can calculate the respective reflection spectrum in a full image operating mode for each of the plurality of image zones. The processing unit can in particular also determine the secondary image data set such that it is modified with respect to the primary image data sets for each of the plurality of image zones. The total image information presented at the electronic viewfinder can thus be modified in this full image operating mode. This is, however, not absolutely necessary. The explained calculation can in particular only be carried out for some image zones, for example when the required calculation time should be reduced.

In accordance with a further embodiment, the electronic viewfinder is selectively at least operable in a standard operating mode or in a filter operating mode, with the control device controlling the electronic viewfinder in the standard operating mode to display one or more respective primary image data sets and to display an image corresponding to the secondary image data set in the filter operating mode. The user can thus select whether he would like to observe the object on the basis of an "unfalsified" primary image data set or whether he prefers a modified version. It is, for example, also conceivable that the image of the secondary image data set is superposed on the image of the primary image data set in a semi-transparent manner.

In accordance with a further embodiment, the control device is configured to operate the electronic viewfinder selectively in a configuration operating mode or in an observation operating mode, with the control device being configured to control the electronic viewfinder in the configuration operating mode for a simultaneous display of a plurality of images that correspond to mutually different secondary image data sets, with a second image data set being selectable from the plurality of images. In the observation operating mode, in contrast, the display of only one image correspond to the selected secondary image data set is provided.

The configuration operating mode thus allows a particularly intuitive option to choose between different observation spectra or modification variants since the corresponding images can be presented simultaneously, for example as "tiles", and can be compared with one another. The user can therefore ideally choose the variant preferred by him in accordance with his individual perception. The electronic viewfinder can e.g. be equipped with a manual operating apparatus for selecting the preferred variant. The user can thus choose particularly comfortably.

An image corresponding to a primary image data set is preferably also displayed in the configuration operating mode so that the user can also carry out the direct comparison with an unmodified version of the primary image data set and can better decide whether the electronic viewfinder is to be operated in the standard operating mode or in the filter operating mode.

The illumination spectrum at which the illumination device transmits the electromagnetic radiation into the recording zone can be variable discretely and/or continuously. A discrete variation of the illumination spectrum can take place, for example, by a simple switchover between different illuminants having respectively different illumination spectra. The illumination spectrum can, however, also be varied by a variation of the electrical feed current by amount. The variation of the feed current additionally opens up the possibility of specifically adapting the illumination spectrum to a respective object. Provided that e.g. specific spectral ranges are particularly important, they can be analyzed particularly easily with correspondingly tailored illumination spectra. The number of illumination spectra can furthermore be considerably increased to improve the accuracy of the approximated reflection spectrum.

In accordance with a preferred embodiment, the illumination device has a plurality of illuminants each having a different illumination spectrum, with the control device being adapted to control the illuminants alternately to discretely vary the illumination spectrum. The cyclic control of the illumination device can thus take place by a simple switching on and off of the individual illuminants. The illuminants are preferably energy-efficient and long-life light emitting diodes (LEDs). The number of illuminants (e.g. individual light emitting diodes or groups of light emitting diodes) preferably amount to two to five, particularly preferably to four. Each illuminant can have a specific color, e.g. red, green, a warm white, or a cold white.

With four illuminants, the cycle frequency, i.e. the number of repeated transmissions of the electromagnetic radiation having the four different illumination spectra and generations of the primary data sets per second, can be in the range of 60 Hz. The frequency can in particular be sufficiently high to minimize the visibility of the changes of the illumination spectra.

As mentioned above, the emission spectrum can in particular be changed with light emitting diodes by varying the electric current (wavelength tunable light emitting diode). A plurality of different illumination spectra can thus be generated by means of the same light emitting diode or group of light emitting diodes, whereby the number of required illuminants and above all the required space for the arrangement of the illuminants can be reduced. The latter is important since only a limited aperture is available for the transmission of the electromagnetic radiation (problems of unwanted shading, for example). An optional fifth illumination spectrum can furthermore be provided in this manner.

In accordance with a further embodiment, the image sensor is a color sensor, with the image sensor having at least two, preferably three or four, mutually different spectral channels or spectral ranges to generate the image signals. The number of spectral channels preferably corresponds to the number of reception spectra, with each spectral channel being associated with exactly one of the reception spectra. The color sensor can in particular have the colors red, green, and blue (RGB) as the spectral channels. The image sensor can be equipped with a color filter matrix, e.g. in accordance with the principle of a Bayer image sensor, for this purpose. A Bayer image sensor can have two like green spectral channels within each image zone (RGBG color filter matrix) or the image sensor has a red spectral channel, a first green spectral channel, a second green spectral channel different from the first green spectral channel, and a blue spectral channel (RG1BG2 color filter matrix). Different arrangements or the spectral channels or combinations of spectral channels are also possible. Alternatively or additionally, a plurality of different image sensors can be used (e.g. as a Foveon sensor). Beam splitters having an edge filter and a plurality of image sensors are furthermore conceivable.

As already explained, each combination of one of the plurality of different illumination spectra with one of the plurality of different reception spectra that occurs within an illumination cycle corresponds to a response function for which the primary image data sets comprise a respective measured value. So that sufficient information is available for a sufficiently exact calculation or approximation of the respective reflection spectrum, at least nine different response functions which are linearly independent of one another should be provided within each illumination cycle in accordance with the studies of the applicant.

These response functions should be selected such that they deliver a measured value differing from zero—if an object having a corresponding reflection capability is examined. It is preferred for this purpose if at least some of the plurality of different illumination spectra, preferably all of them, overlap with all of the plurality of different reception spectra. In other words, the (spectral) extent range for at least some of the illumination spectra falls in the extent range of the reference spectra. It can be ensured in this manner that a plurality of mutually different reception spectra are present and can be evaluated for at least some of the illumination spectra, preferably for every illumination spectrum, said reception spectra detecting a reflection of the radiation transmitted with this illumination spectrum. The respective bandwidths of the plurality of different illumination spectra can in particular overlap with the respective bandwidth of the plurality of different reception spectra. The respective spectrally dominant ranges that represent particularly relevant spectral portions with respect to their amounts can thus overlap. The accuracy in the calculation of the reflection spectrum can hereby typically be increased.

In accordance with a further embodiment, the respective reflection spectrum has at least one spectral range that is outside the plurality of different illumination spectra and reception spectra. In other words, the reflection spectrum can, as initially mentioned, extend over spectral ranges that do not directly coincide with the different reception spectra or illumination spectra. In this manner, despite the use of an (only) multispectrally resolving image sensor, the possibility is opened up of determining a hyperspectrally resolved reflection spectrum.

Said computing rule for calculating the respective reflection spectrum can be determined once at the manufacturer's and then stored in the memory. Alternatively or additionally, the microscope can be configured to determine the computing rule. In accordance with such an embodiment, the control device can e.g. be configured to determine the computing rule in an initializing operating mode of the microscope and then to save it in the memory. In this manner, the specific optical conditions, e.g. in an operating theater, can be ideally taken into account so that the determined computing rule is particularly well suited to approximate the reflection spectrum with minimal error. Alternatively to the initialization operating mode, an observation operating mode can be provided in which the stored computing rule is used.

The computing rule can be an internal function, in particular a fixed function, with which the reflection spectrum is calculated as required. A pre-calculation can be carried out to minimize the computing effort, with required calculation results only having to be read from a table ("look-up table") in normal operation of the microscope.

In accordance with a preferred embodiment, the computing rule is based on a plurality of principal components of a principal component analysis of reflection spectra, with the number of principal components being the same as or smaller than the product of the number of reception spectra and the number of illumination spectra of a cycle. In the event that the number of principal components is smaller than the product of the number of reception spectra and the number of illumination spectra, a certain piece of "redundant information" results since said product for carrying out the computing rule (solution of the equation system) only has to be the same as the number of principal components if no linear dependencies are present. Ultimately, an overdetermined equation system is present whose degree of overdetermination or redundancy is used to evaluate the validity of the solution as will be explained in the following.

The computing rule can be derived as follows, by way of example.

A principal component analysis is carried out on the basis of a plurality of known reflection spectra. The 24 Macbeth ColorChecker reflection spectra (n=24) can e.g. be considered as known reflection spectra that can each comprise 81 values from 380 nm to 780 nm in steps of 5 nm (m=81). The reflection spectra can be arranged in a matrix R of the dimensions 81×24 on the basis of which a singular value decomposition can be carried out with matrices U (81×81), Σ (81×24), and V (24×24):

$$R = U\Sigma V^T,$$

where $u_j=(U_{ij})$, i,j=1, 2, ... 81 is the orthonormal base of the 81-dimensional vector space of the real numbers acquired by the singular value decomposition. Each (reflection) spectrum v tabulated in the same space can then be described as:

$$v = \sum_{i=1}^{81} v_i u_i \text{ where } v_i = \langle v, u_i \rangle,$$

with a reduced number of the 81 sum terms being sufficient to approximate the spectrum v with a high accuracy. The first 5 to 15 sum terms, particularly preferably the first 9 sum terms, (or principal components $u_i$) are in particular sufficient to approximate the spectrum v with sufficient accuracy. An exact approximation based on the first 5 to 15 sum terms can in particular be carried out when the spectrum v typically has a smooth extent over the frequency. This can in particular be the case with specific groups of reflection spectra, e.g. those of organic tissue types.

Starting from the first 9 principal components, an unknown reflection spectrum v should be estimated. For this purpose, response functions $r_j$, j=1, 2, ... 12 of the image sensor are present for each image zone and are calculated by multiplying each of the 4 illumination spectra by each of the 3 reception spectra ("sensor sensitivities"). Furthermore, the images signals w=($w_j$), j=1, 2, ... 12 are present that were determined for estimating the unknown spectrum v and result as follows mathematically:

$$w_j = \sum_{i=1}^{9} \langle r_j, u_i \rangle v_i \approx \langle r_j, v \rangle.$$

The following overdetermined linear equation system is obtained with V=($\langle r_j, u_i \rangle$):

$$Vv=w.$$

The approximated spectrum $\tilde{v}$ results as:

$$\tilde{v}=V^+w,$$

where $V^+$ is the Moore-Penrose inverse (pseudoinverse) of the matrix V that can be calculated using a singular value decomposition of V. A statement on the validity of the estimate can additionally be made using the level of the singular values of V. For example, the equation system Vv=w could be underdetermined when V approximately does not have full status and one or more singular values of V are therefore very small. In this case, the response functions are, e.g. due to linearly dependent columns of V, not necessarily well suited to separate the influences of the principal components in the sense of an estimate that is as unambiguous as possible, i.e. a valid estimate. A determination can therefore be made on the basis of the singular values as to the extent to which the estimate of the unknown spectrum can be considered as plausible at least on the basis of mathematical aspects. Conversely, response functions that are as linearly independent as possible or are mutually different, i.e. linearly independent columns of V, are advantageous for a valid estimate.

The computing rule of the microscope in accordance with the invention can in particular comprise the matrix $V^+$ to determine the reflection spectrum on the basis of the image signals of the observed image zone while taking account of all the plurality of primary image data sets of a cycle.

In general terms, this means that said computing rule can comprise a multiplication of the primary image data sets generated in an illumination cycle for the plurality of different illumination spectra by a matrix that has a predefined number of independent columns. This predetermined number preferably amounts to at least nine, with the number being sufficient to achieve a sufficiently high accuracy in the (approximate) calculation of the reflection spectrum, on the one hand, and with the number of required illumination spectra per illumination cycle also being able to be kept small with this number of independent columns of the matrix, on the other hand.

Said matrix can have a number of rows that is greater than the number of independent columns to provide a redundancy of the determined information, as explained. In the example of nine independent columns, twelve rows can be provided, which can correspond to the combination of four illumination spectra with three reception spectra (or vice versa).

In accordance with an embodiment, the microscope can furthermore have an electronic image stabilization device that is configured to compensate differences in the recording conditions that occur within an illumination cycle on generating the primary image data sets. Falsifications can hereby be avoided or largely suppressed that can occur in that the recording conditions change between the generation of the primary image data sets for different illumination spectra. Such changed recording conditions can, for example, comprise a spatial offset of the image of the examined object on the image sensor (e.g. due to a vibration of the microscope or a movement of the object), with such a spatial offset being able to be compensated by calculation, for example by image recognition. In addition, such changed recording conditions can, for example, also comprise a blur, a rotation, or an enlargement.

In accordance with a preferred embodiment, the microscope is configured as a stereo microscope. In this embodiment, the required computing effort can be reduced when the determination of the reflection spectrum is only carried out for one of the two stereo channels. The modification with respect to the primary image data sets of one stereo channel can furthermore be used in a corresponding manner on the other stereo channel, whereby the computing effort is only slightly higher in comparison with a monoscopic microscope.

The invention will be explained in the following with reference to the enclosed drawings, in which.

Figure 1:
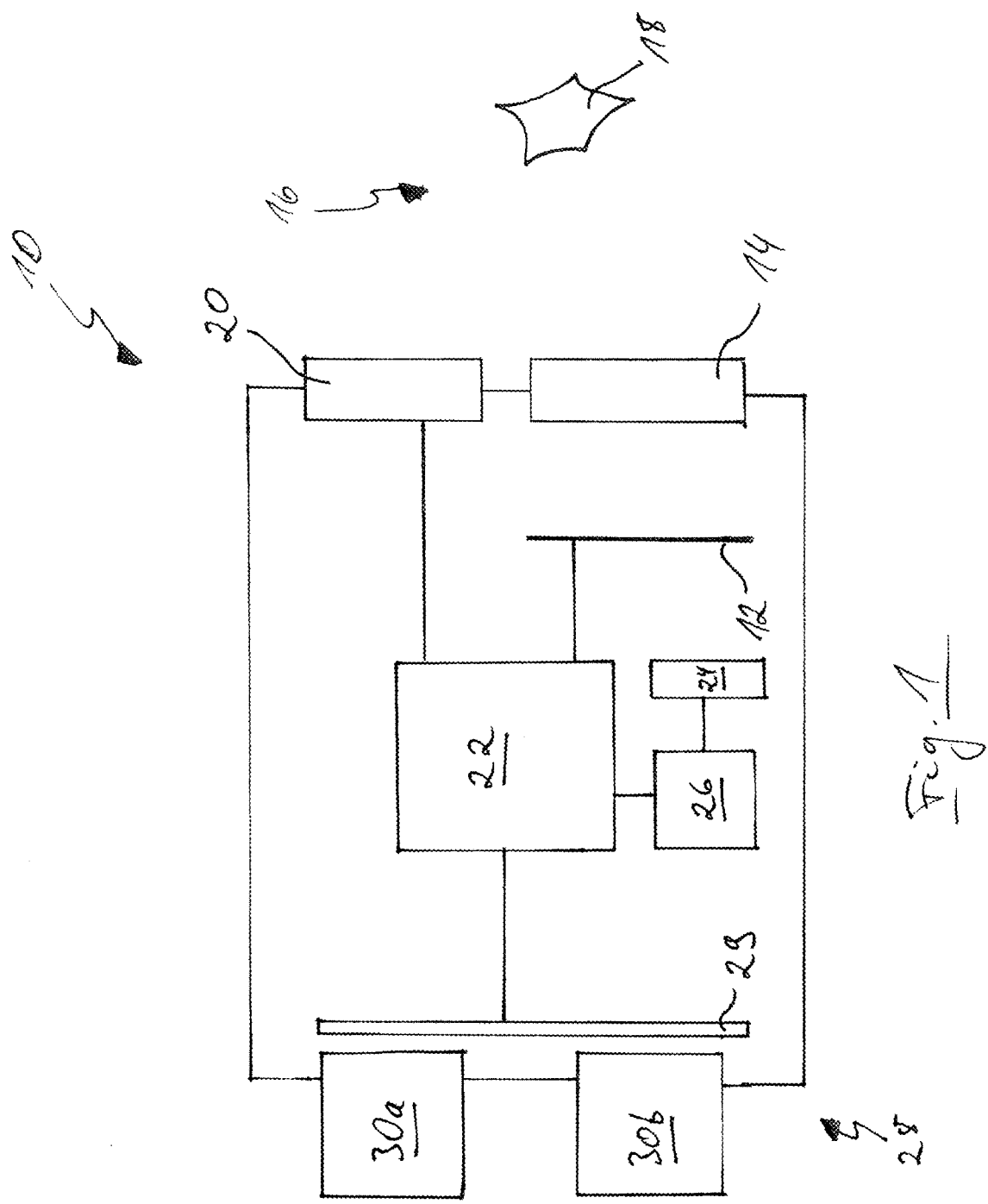
FIG. 1 shows a schematic block diagram of an electronic microscope.

An electronic microscope 10 schematically shown in FIG. 1 (specifically an operating microscope here) comprises a electronic image sensor 12 for generating primary image data sets. The electronic image data set 12 is configured to generate image signals in dependence on an application of electromagnetic radiation for a plurality of image zones that can each comprise a picture element or a group of mutually adjacent picture elements. The image signals generated by the image sensor 12 for each image zone correspond to a plurality of different reception spectra, with each primary image data set for the plurality of image zones respectively comprising at least one image signal of each of the plurality of reception spectra. An imaging optics 14 is furthermore provided for generating an image of an object 18 arranged in a recording zone 16 of the microscope 10 (e.g. a surgical wound) on the image sensor 12. The imaging optics 14 can be variably adjustable.

An illumination device 20 of the microscope 10 is configured to transmit electromagnetic radiation having a variable illumination spectrum into the recording zone 16. The illumination device 20 can in particular have four LED illuminants that, in the event of being controlled, output light with a defined color, i.e. with a defined illumination spectrum.

The microscope 10 further comprises a control device 22 that is configured to control the illumination device 20 to make a repeating transmission of the electromagnetic radiation having a plurality of different illumination spectra in a respective illumination cycle and to control the image sensor 12 to generate a respective primary image data set for each of the plurality of different illumination spectra. The image sensor 12 thus generates a plurality of image signals whose number corresponds to the number of said reception spectra for each image zone and for each illumination spectrum.

A computing rule is stored in a memory 24 and represents a reflection spectrum of an observed respective image zone in dependence on the image signals that have been generated by the image sensor 12 for the observed respective image zone for each of the plurality of different reception spectra with respect to each of the plurality of different illumination spectra. The memory 24 is connected to a processing unit 26 that is configured to calculate the reflection spectrum for some or all of the plurality of image zones from the primary image data sets generated for the plurality of different illumination spectra in accordance with the stored computing rule and, starting from the primary image data sets generated for the plurality of different illumination spectra, to determine at least one secondary image data set that is at least partly modified with respect to the primary image data sets in dependence on the calculated reflection spectrum. The calculated reflection spectrum thus represents the spectral dependence of the reflection capability of the object 18 arranged in the recording zone 16 in an object zone that corresponds to the respective image zone in accordance with the optical imaging by means of the imaging optics 14.

The control device 22 is configured to control an electronic viewfinder 28 of the microscope 10 to display an image corresponding to the secondary image data set. Specifically, the control device 22 controls an electronic display apparatus 29 that can be observed through eyepieces 30a, 30b by a user, not shown, of the microscope 10.

Figure 2:
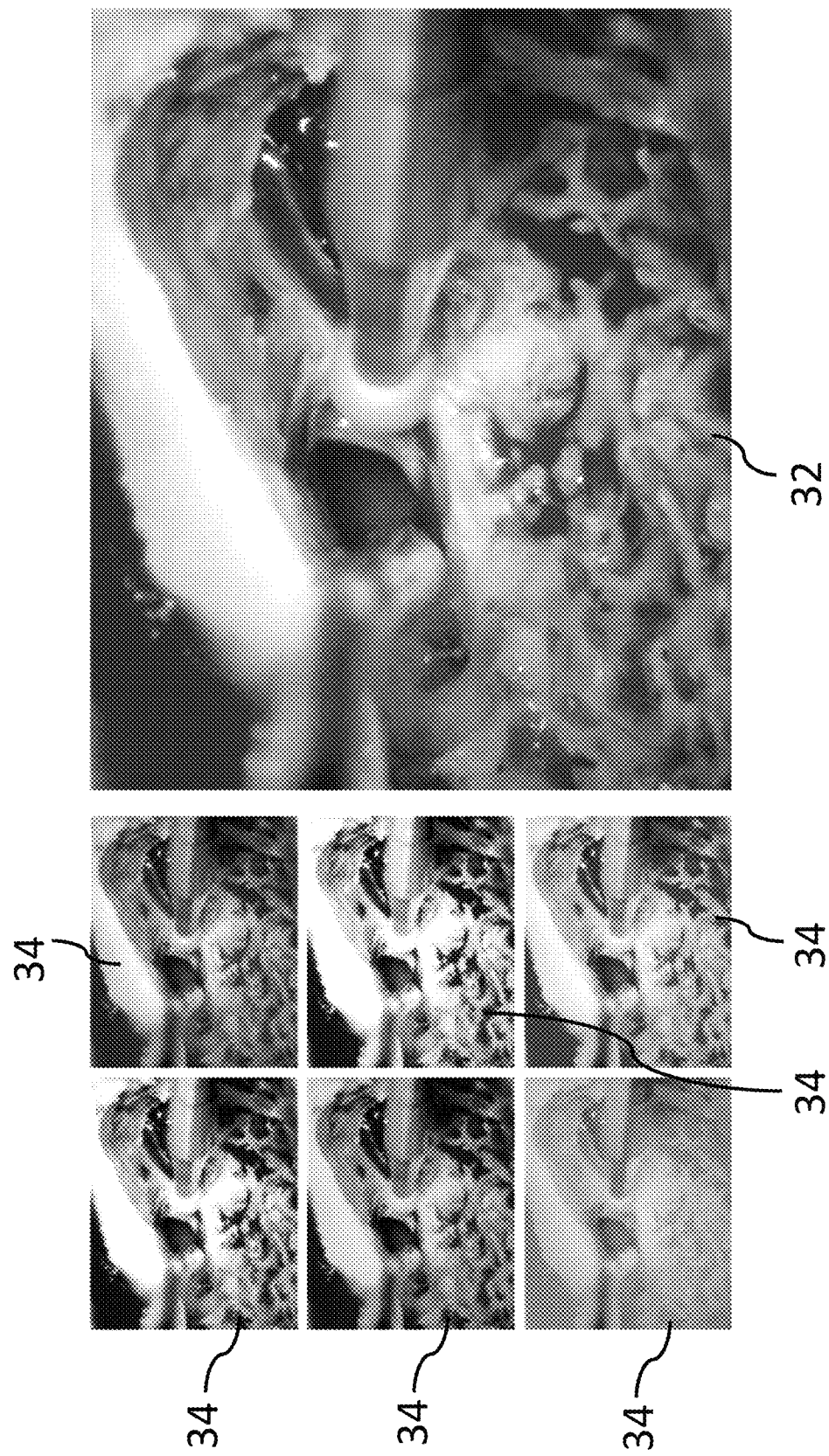
FIG. 2 shows an image displayed at an electronic viewfinder of the microscope of FIG. 1.

A display image is shown in FIG. 2 that can be displayed to the user in a configuration operating mode of the electronic viewfinder 28. An image 32 is displayed on the right hand side that corresponds to one of the primary image data sets generated for an illumination cycle or to a combination of a plurality or all of the primary image dates sets generated for an illumination cycle. The image 32 can in particular be displayed in a true-color representation. A plurality of images 34 are displayed on the left hand side that correspond to mutually different secondary image data sets. As can be recognized, the images 34 are presented to the user as spectrally differently filtered versions of the image 32 that permit a respective subjectively varied observation of the object 18 (a surgical wound here). The different images 34 or secondary image data sets each correspond to a spectral portion, that is to a bandpass filtering, of the calculated (complete) reflection spectrum in the respective image zone. The different images 34 can be displayed in a color representation that at least substantially corresponds to the respective spectral portion or in different false color representations, or in a respective gray scale representation. The user can select the image 34 preferred by him from the plurality of images 34 (for example by means of a selection device not shown in any more detail, e.g. by a mouse click) to select an associated secondary image data set. A filter data set is hereby ultimately selected with which a respective primary image data set should be modified.

The user can then switch into an observation operating mode in which only the image corresponding to the selected secondary image data set is displayed, in particular in a size adapted to the size of the display apparatus 29. The user can in this manner select the ideal modification variant for his subjective needs or ideal for the circumstances, whereby the quality of the surgery carried out can ultimately be improved.

Alternatively to such a user-controlled selection, the selection of a secondary image data set (without a previous representation at the electronic viewfinder 29 in accordance with FIG. 2) can also take place automatically on the basis of an evaluation of one or more calculated reflection spectra. The use of the microscope can hereby be made even more comfortable. A reflection spectrum calculated for a respective image zone can in particular be compared with a plurality of known reflection spectra stored in the memory 24 to identify that know reflection spectrum that corresponds to the calculated reflection spectrum. This can be done, for example, by means of a mathematical approximation method. A respective rule in accordance with which the primary image data sets are modified to determine the secondary image data set can additionally be stored in the memory 24 for each of the known reflection spectra. A specific type of tissue that corresponds to the identified reflection spectrum can hereby, for example, be represented better at the electronic viewfinder 29.

In accordance with an expanded embodiment, it is also possible to identify a plurality of different types of tissue in this manner and to represent them in different manners, for example by a different coloring. Alternatively or additionally, it is also possible to determine a probability value in connection with said identification of a known reflection spectrum, said probability value representing the probability that the identified reflection spectrum actually corresponds to the calculated reflection spectrum. Different determined probability values can thus be used to color the respective image zones in corresponding different colors.

Differing from the illustration in FIG. 2, it is also possible only to modify a secondary image data set for some image zones (i.e. not for all of them) with respect to the primary image data sets and to display them at the electronic viewfinder 29 in a correspondingly modified manner of representation. These image zones can, for example, form a contiguous areal zone or a border of an areal zone. Such an areal zone can, for example, correspond to an identified type of tissue within the image of the object 18. The respective image zones can, for example, be color-offset with respect to the further image zones.

REFERENCE NUMERAL LIST 10 microscope
12 image sensor
14 imaging optics
16 recording zone
18 object
20 illumination device
22 control device
24 memory
26 processing unit
28 electronic viewfinder
29 display apparatus
30a eyepiece
30b eyepiece
32 image
34 image

The invention claimed is:

1. An electronic microscope that is an operating microscope, comprising:
at least one electronic image sensor (12) for generating primary image data sets, wherein the at least one electronic image sensor (12) is configured to generate image signals that correspond to a plurality of different reception spectra, and wherein each primary image data respectively comprises at least one image signal of each of the plurality of reception spectra for a plurality of image zones;
an imaging optics (14) for generating an image of an object (18) arranged in a recording zone (16) of the microscope on the at least one image sensor (12);
an electronic viewfinder (28);
an illumination device (20) that is configured to transmit electromagnetic radiation having a variable illumination spectrum into the recording zone (16);
a computer processor; and
a memory coupled to the computer processor having instructions stored thereon which, when executed by the computer processor, cause the computer processor to perform a method comprising:
controlling the illumination device (20) to make a cyclically repeating transmission of the electromagnetic radiation having a plurality of different illumination spectra and controlling the at least one image sensor (12) to generate a respective primary image data set for each of the plurality of different illumination spectra;
storing a computing rule which represents a reflection spectrum of an observed respective image zone in dependence on the image signals that have been generated for the observed image zone for each of the plurality of different reception spectra with respect to each of the plurality of different illumination spectra; and
calculating the respective reflection spectrum for at least some of the plurality of image zones from the primary image data sets generated for the plurality of different illumination spectra in accordance with the stored computing rule and, starting from the primary image data sets generated for the plurality of different illumination spectra, determining in dependence on the respective calculated reflection spectra at least one secondary image data set that is at least partly modified with respect to the primary image data sets;
controlling the electronic viewfinder (28) for displaying an image corresponding to the at least one secondary image data set, and
wherein the electronic microscope has a selection device, with a desired observation spectrum that is different from the illumination spectra being selectable by means of the selection device, and with the at least one secondary image data set being modified with respect to the primary image data sets on the basis of the selected observation spectrum,
where in the method further comprises evaluating the respective calculated reflection spectrum with respect to at least one property of the object (18), with the at least one secondary image data set being modified with respect to the primary image data sets on the basis of the at least one evaluated object property, and with the selection device being adapted to select the observation spectrum automatically on the basis of the at least one evaluated object property;
wherein the at least one secondary image data set for the at least some image zones represents the reflection capability of the object (18) arranged in the recording zone (16) within the selected observation spectrum.

2. An electronic microscope in accordance with claim 1, wherein the method further comprises evaluating the respective calculated reflection spectrum with respect to at least one property of the object (18), and with the at least one secondary image data set being modified with respect to the primary image data sets on the basis of the at least one evaluated object property.

3. An electronic microscope in accordance with claim 2, wherein the at least one secondary image data set for the at least some image zones represent the at least one evaluated object property.

4. An electronic microscope in accordance with claim 1, wherein the selection device is actuable by the user during the operation of the electronic microscope.

5. An electronic microscope in accordance with claim 1, wherein the method further comprises calculating the respective reflection spectrum for each of the plurality of image zones in a full image operating mode.

6. An electronic microscope in accordance with claim 1, wherein the electronic viewfinder (28) is selectively operable in at least a standard operating mode or in a filter operating mode, with the method further comprises controlling the electronic viewfinder (28) to display an image corresponding to one or more respective primary image data sets in the standard operating mode; and to display an image corresponding to the at least one secondary image data set in the filter operating mode.

7. An electronic microscope in accordance with claim 1, wherein the method further comprises operating the electronic viewfinder (28) selectively in a configuration operating mode or in an observation operating mode, and controlling the electronic viewfinder (28) in the configuration operating mode to simultaneously display a plurality of images that correspond to mutually different secondary image data sets, with a secondary image data set being selectable from the plurality of images; and controlling the electronic viewfinder (28) in the observation operating mode to display only an image corresponding to the selected secondary image data set.

8. An electronic microscope in accordance with claim 1, wherein the illumination spectrum is discretely variable and/or continuously variable.

9. An electronic microscope in accordance with claim 1, wherein the illumination device (20) has a plurality of illuminants each having a different illumination spectrum, and the method comprises controlling the illuminants alternately to discretely vary the illumination spectrum.

10. An electronic microscope in accordance with claim 1, wherein the illumination device (20) has at least one light emitting diode whose illumination spectrum is variable by a different energy supply.

11. An electronic microscope in accordance with claim 1, wherein the at least one image sensor (12) is a color sensor; and wherein the image sensor (12) has at least two mutually different spectral channels to generate the image signals.

12. An electronic microscope in accordance with claim 1, wherein the at least one image sensor (12) has a red spectral channel, a first green spectral channel, a second green spectral channel differing from the first green spectral channel, and a blue spectral channel.

13. An electronic microscope in accordance with claim 1, wherein every combination of one of the plurality of different illumination spectra having one of the plurality of different reception spectra corresponds to a response function, with at least nine different response functions that are linearly independent of one another being provided within each illumination cycle.

14. An electronic microscope in accordance with claim 1, wherein at least some of the plurality of different illumination spectra overlap with all of the plurality of different reception spectra.

15. An electronic microscope in accordance with claim 1, wherein all of the plurality of different illumination spectra overlap with all of the plurality of different reception spectra.

16. An electronic microscope in accordance with claim 1, wherein the respective calculated reflection spectrum has at least one spectral range that is outside the plurality of different illumination spectra and reception spectra.

17. An electronic microscope in accordance with claim 1, wherein the method comprises determining the computing rule in an initializing operating mode of the microscope and then saving the computing rule in the memory (24).

18. An electronic microscope in accordance with claim 1, wherein the computing rule is based on a plurality of principal components of a principal component analysis of a plurality of reflection spectra, with the number of principal components being the same as or smaller than the product of the number of reception spectra and the number of illumination spectra of an illumination cycle.

19. An electronic microscope in accordance with claim 1, wherein the computing rule comprises a multiplication of the primary image data sets generated for the plurality of different illumination spectra in an illumination cycle by a matrix that has at least nine independent columns.

20. An electronic microscope in accordance with claim 1, wherein the microscope furthermore has an electronic image stabilization device that is configured to compensate differences in the recording conditions that occur within an illumination cycle on generating the primary image data sets.

* * * * *

UNITED STATES PATENT AND TRADEMARK OFFICE
CERTIFICATE OF CORRECTION

| | |
|---|---|
| PATENT NO. | : 10,849,505 B2 |
| APPLICATION NO. | : 15/847607 |
| DATED | : December 1, 2020 |
| INVENTOR(S) | : Julius Muschaweck et al. |

It is certified that error appears in the above-identified patent and that said Letters Patent is hereby corrected as shown below:

On the Title Page
Under item (73) Assignee:
"Arnold & Richter Cine Technik GmbH & Co. Betriebs KG, München (DE)"
Should be changed to:
--ARRI Medical GmbH, München (DE)--

Signed and Sealed this
Third Day of May, 2022

Katherine Kelly Vidal
*Director of the United States Patent and Trademark Office*